US012331028B2

(12) United States Patent
Panchal et al.

(10) Patent No.: US 12,331,028 B2
(45) Date of Patent: *Jun. 17, 2025

(54) PROCESS FOR PREPARATION OF ANTHRANILAMIDES

(71) Applicant: UPL LTD, Haldia (IN)

(72) Inventors: Digish Manubhai Panchal, Mumbai (IN); Jigar Kantilal Desai, Mumbai (IN); Jaidev Rajnikant Shroff, Mumbai (IN); Vikram Rajnikant Shroff, Dubai (AE)

(73) Assignee: UPL LTD, Haldia (IN)

( * ) Notice: Subject to any disclaimer, the term of this patent is extended or adjusted under 35 U.S.C. 154(b) by 758 days.

This patent is subject to a terminal disclaimer.

(21) Appl. No.: 17/311,467

(22) PCT Filed: Dec. 6, 2019

(86) PCT No.: PCT/IB2019/060508
§ 371 (c)(1),
(2) Date: Jun. 7, 2021

(87) PCT Pub. No.: WO2020/136480
PCT Pub. Date: Jul. 2, 2020

(65) Prior Publication Data
US 2022/0024892 A1 Jan. 27, 2022

(30) Foreign Application Priority Data
Dec. 24, 2018 (IN) .............................. 201831048884

(51) Int. Cl.
*C07D 401/04* (2006.01)
(52) U.S. Cl.
CPC ................................. *C07D 401/04* (2013.01)
(58) Field of Classification Search
CPC .................................................. C07D 401/04
See application file for complete search history.

(56) References Cited

U.S. PATENT DOCUMENTS

| 7,232,836 B2 | 6/2007 | Lahm et al. |
| 7,247,647 B2 | 7/2007 | Hughes et al. |
| 7,842,720 B2 * | 11/2010 | Elsohly ............... A61P 31/00 549/348 |
| 2010/0256195 A1 | 10/2010 | Fischer et al. |
| 2011/0046186 A1 | 2/2011 | Li et al. |
| 2011/0178109 A1 * | 7/2011 | Natsuhara ............. A01N 43/56 514/269 |
| 2015/0322037 A1 * | 11/2015 | Wang ................ C07D 413/14 546/275.4 |

FOREIGN PATENT DOCUMENTS

| JP | WO 2011062291 | * | 5/2001 | ............ A01N 43/56 |
| WO | 2006068669 A1 | | 6/2006 | |
| WO | WO 2006/068669 | * | 6/2006 | ............ A01N 43/56 |
| WO | 2011062291 A1 | | 5/2011 | |
| WO | 2012103436 A1 | | 8/2012 | |
| WO | 2015055447 A1 | | 4/2015 | |

OTHER PUBLICATIONS

Bartlett "Exploiting Chemical Diversity for Drug Discovery" Edited by Paul A Bartlett and Michael Entzeroth, the Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/ZRegistry (CAS RegistrySM) Sep. 2016 2 pages.*
Armarego, Purification of Laboratory Chemicals, Sixth Edition, Chapter 1, 2009.*
Anonymous; "Pesticide Fact Sheet—Chlorantraniliprole"; United States Environmental Protection Agency Office of Prevention, Pesticides and Toxic Substances [Pesticide Fact Sheet]; available online at www3.epa.gov/pesticides/chem_search/reg_actions/registration/fs_PC-090100_01-Apr-08.pdf, retrieved on Jan. 31, 2020; 77 pages.
International Search Report and Written Opinion for International Application PCT/IB2019/060508; International Filing Date: Dec. 6, 2019; Date of Mailing: Feb. 20, 2020; 18 pages.

* cited by examiner

*Primary Examiner* — Nizal S Chandrakumar
(74) *Attorney, Agent, or Firm* — CANTOR COLBURN LLP

(57) ABSTRACT

The present invention provides a process for preparation and purification of anthranilamides.

2 Claims, No Drawings

PROCESS FOR PREPARATION OF ANTHRANILAMIDES

CROSS REFERENCE TO RELATED APPLICATIONS

This application is a National Stage application of PCT/IB2019/060508, filed Dec. 6, 2019, which claims priority to Indian Patent Application number 201831048884, filed Dec. 24, 2018, both of which are incorporated by reference in their entirety herein.

TECHNICAL FIELD OF THE INVENTION

The present invention relates to the preparation of Anthranilamides. The present invention further provides anthranilamide that is free from impurities. Particularly, the present invention provides a process for purifying anthranilamides that is free from impurities.

BACKGROUND OF THE INVENTION

Effective control of insect pest such as arthropods is essential for crop safety. Arthropods are an important class of pests which cause huge damage to crop and household every year around the world. Anthranilamides are a new class of compounds with extremely potent insecticidal activity. These nitrogen-containing aromatic compounds selectively act on targeted ryanodine receptors in insects. Ryanodine receptors form calcium ion channels which are responsible for muscle function.

Examples of insecticidal anthranilamides are cyantraniliprole, chlorantraniliprole, cyclaniliprole, tetrachlorantraniliprole and tetraniliprole. Chlorantraniliprole is a highly potent and selective activator of insect ryanodine receptor with exceptional activity on a broad range of Lepidoptera. It controls a wide range of chewing pests (primarily Lepidoptera, but also some Coleoptera, Diptera and Isoptera species) in a broad range of crops, including fruit, vegetables, vines, cotton, sugar cane, rice and grass.

U.S. Pat. No. 7,232,836 discloses the preparation of chlorantraniliprole represented as compound of Formula IV (Scheme I).

Scheme I

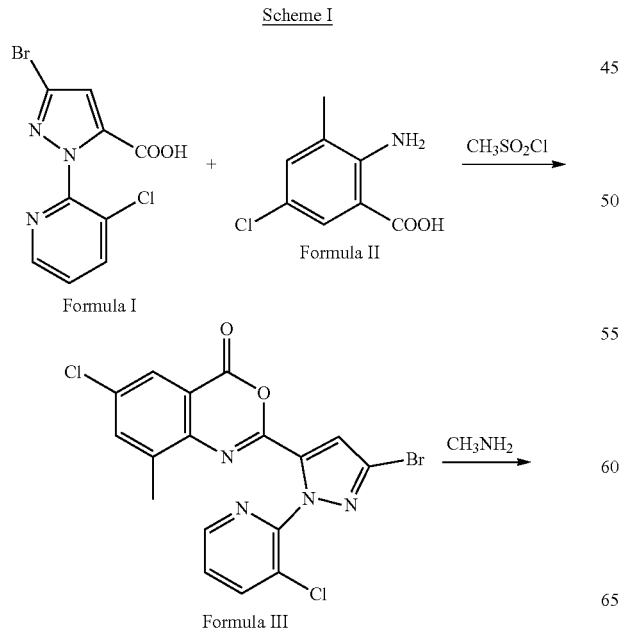

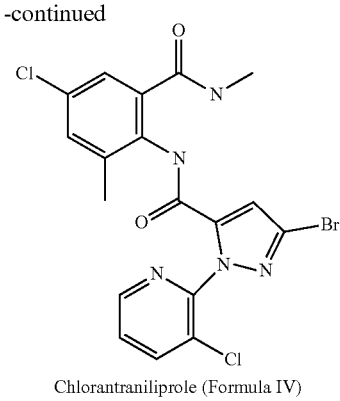

Chlorantraniliprole (Formula IV)

Intermediate 3-bromo-1-(3-chloropyridin-2-yl)-1H-pyrazole-5-carboxylic acid is represented as compound of Formula I and intermediate 2-amino-5-chloro-3-methylbenzoic acid is represented as compound of Formula II. 2-[3-bromo-1-(3-chloropyridin-2-yl)-1H-pyrazol-5-yl]-6-chloro-8-methyl-4H-3,1-benzoxazin-4-one is referred to as compound of Formula III.

U.S. Pat. No. 7,247,647 discloses the preparation of cyantraniliprole (Formula represented as compound of Formula VII (Scheme II).

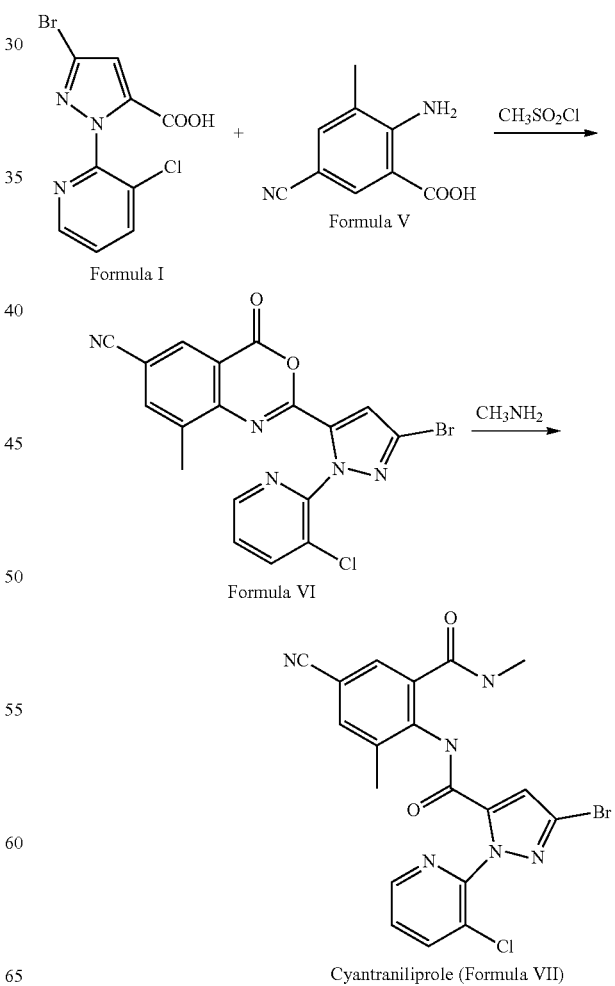

Cyantraniliprole (Formula VII)

Intermediate 3-bromo-1-(3-chloropyridin-2-yl)-1H-pyrazole-5-carboxylic acid is represented as compound of Formula I and intermediate 2-amino-5-cyano-3-methylbenzoic acid is represented as compound of Formula V. 2-[3-bromo-1-(3-chloropyridin-2-yl)-1H-pyrazol-5-yl]-6-cyano-8-methyl-4H-3,1-benzoxazin-4-one is referred to as compound of Formula VI.

Inventors of the present invention noted that compound of Formula III is not physically stable enough to undergo appropriate purification. It has been further noted that impure compound of Formula III on further reaction with methyl amine, leads to chlorantraniliprole with inconsistent physical and chemical properties which in turn leads to ineffective product for the intended use.

Further, it has been observed that low solubility of anthranilamides in water and/or organic solvents makes it challenging to conduct appropriate purification processes.

Therefore, there is a need to develop improved preparation and purification methods for anthranilamides.

OBJECTS OF THE INVENTION

It is an object of the present invention to provide anthranilamides that is free of impurities.

It is another object of the present invention to provide a process for preparation of anthranilamides.

It is yet another object of the present invention to provide a process for preparing chlorantraniliprole that is free from impurities.

SUMMARY OF THE INVENTION

The present invention provides compounds of Formula (A) that are substantially free from impurities:

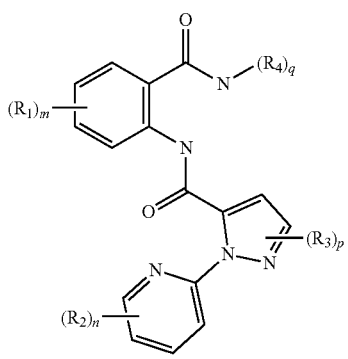

Formula A wherein $R_1$, $R_2$, $R_3$ and $R_4$ can be independently a hydrogen, halogen, cyano, amino, N-thio derivatives, hydroxyl, unsubstituted or substituted linear or branched ($C_1$-$C_{10}$) alkyl or cycloalkyl, heterocyclic unsubstituted or substituted with halogen, cyano, amino, hydorxyl or linear or branched ($C_1$-$C_{10}$) alkyl and wherein m, n, p and q can be 0, 1, 2, or 3.

The present invention provides a process for purifying compound of Formula A,

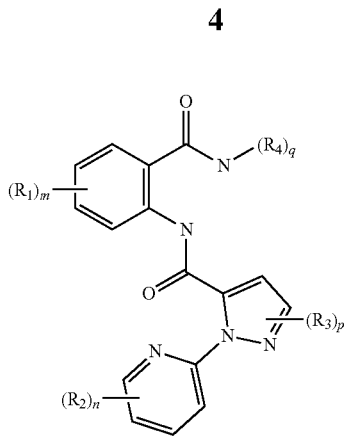

Formula A wherein $R_1$, $R_2$, $R_3$ and $R_4$ can be independently a hydrogen, halogen, cyano, amino, N-thio derivatives, hydroxyl, unsubstituted or substituted linear or branched ($C_1$-$C_{10}$) alkyl or cycloalkyl, heterocyclic unsubstituted or substituted with halogen, cyano, amino, hydroxyl or linear or branched ($C_1$-$C_{10}$) alkyl and wherein m, n, p and q can be 0, 1, 2, or 3;

said process comprising purifying the compound of formula A from an aqueous slurry comprising said compound of formula A.

The present invention provides a process for purifying compound of Formula A,

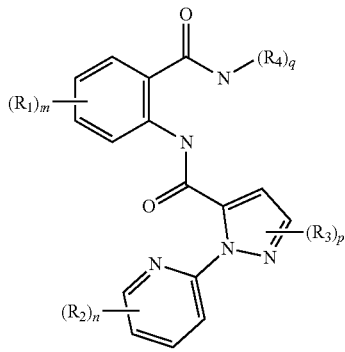

Formula A wherein $R_1$, $R_2$, $R_3$ and $R_4$ can be independently a hydrogen, halogen, cyano, amino, N-thio derivatives, hydroxyl, unsubstituted or substituted linear or branched ($C_1$-$C_{10}$) alkyl or cycloalkyl, heterocyclic unsubstituted or substituted with halogen, cyano, amino, hydroxyl or linear or branched ($C_1$-$C_{10}$) alkyl and wherein m, n, p and q can be 0, 1, 2, or 3;

said process comprising the steps of:
a) feeding a reaction product mixture comprising compound of Formula A into a reactor;
b) preparing a slurry of the mixture in aqueous conditions;
c) stirring the slurry for a pre-determined time;
d) separating solids;
e) optionally repeating steps b), c) and d); and
f) drying to get purified compound of Formula A.

The present invention further provides chlorantraniliprole substantially free of impurities.

The present invention provides a process for purifying chlorantraniliprole, said process comprising purifying Chlorantraniliprole from an aqueous slurry comprising Chlorantraniliprole.

The present invention provides a process for purifying chlorantraniliprole, said process comprising the steps of:
- a) feeding a reaction product mixture comprising chlorantraniliprole into a reactor;
- b) preparing a slurry of the mixture in aqueous conditions;
- c) stirring the slurry for a pre-determined time;
- d) separating solids;
- e) optionally repeating steps b), c) and d); and
- f) drying to get purified Chlorantraniliprole.

The present invention provides a process preparing chlorantraniliprole that is free from impurities, said process comprising purifying Chlorantraniliprole from an aqueous slurry comprising the reaction product of the compound of formula III with methylamine.

The present invention provides a process preparing chlorantraniliprole that is free from impurities, said process comprising the steps of:
- a) reacting compound of Formula III with methyl amine in an organic solvent;
- b) separating and collecting solids;
- c) preparing a slurry of step b) product in aqueous conditions;
- d) stirring the slurry for a pre-determined time;
- e) separating and collecting solids;
- f) optionally repeating steps c), d) and e); and
- g) drying to get chlorantraniliprole substantially free from impurities.

The present invention provides a process for preparing chlorantraniliprole that is substantially free from impurities wherein purification of compound of Formula III is not essential.

The present invention provides a process for preparing chlorantraniliprole that is substantially free from impurities, said process comprising purifying Chlorantraniliprole from an aqueous slurry, said aqueous slurry comprising a hydrophilic solvent admixed with the reaction product of a compound of formula III with methylamine.

The present invention provides a process for preparing chlorantraniliprole that is substantially free from impurities, said process comprising the steps of:
- a) preparing compound of Formula III by reacting compound of Formula I and compound of Formula II in an organic solvent;
- b) optionally purifying compound of Formula III;
- c) reacting compound of Formula III with methyl amine in an organic solvent;
- d) separating and collecting solids;
- e) preparing a slurry of step d) product in aqueous conditions;
- f) stirring the slurry for a pre-determined time;
- g) separating and collecting solids;
- h) optionally repeating steps e), f) and g); and
- i) drying to get chlorantraniliprole free from impurities.

The present invention provides a process for purifying cyantraniliprole, said process comprising purifying cyantraniliprole from an aqueous slurry of cyantraniliprole.

The present invention provides a process for purifying cyantraniliprole said process comprising the steps of:
- a) feeding a reaction product mixture comprising cyantraniliprole into a reactor;
- b) preparing a slurry of the mixture in aqueous conditions;
- c) stirring the slurry for a pre-determined time;
- d) separating solids;
- e) optionally repeating steps b), c) and d); and
- f) drying to get purified cyantraniliprole.

The present invention further provides a process for preparing cyantraniliprole that is free from impurities, said process comprising the steps of:
- a) reacting compound of Formula VI with methyl amine in an organic solvent;
- b) separating and collecting solids;
- c) preparing a slurry of step b) product in aqueous conditions;
- d) stirring the slurry for a pre-determined time;
- e) separating and collecting solids;
- f) optionally repeating steps c), d) and e); and
- g) drying to get cyantraniliprole substantially free from impurities.

The present invention further provides a process for preparing cyantraniliprole said process comprising purifying cyantraniliprole from an aqueous slurry, said aqueous slurry comprising a hydrophilic solvent admixed with the reaction product of a compound of formula VI with methylamine.

DETAILED DESCRIPTION

It has been noted that many of the anthranilamides represented by general structure of Formula A have low solubility in water or in other hydrophilic solvents due to which isolation and purification of the compound is troublesome. Despite their low solubility in water and other hydrophilic solvents, it has been surprisingly found by the present inventors that substantially pure anthranilamides i.e. which is substantially free of impurities, could be prepared by purifying the crude reaction product of the compound of formula III with methylamine, out of an aqueous slurry. Based on this finding, it has been made possible by the present inventors to provide insecticidal anthranilamides that is free from impurities and to a process for preparing such substantially pure anthranilamides.

Chlorantraniliprole is an example of such anthranilamides which is difficult to prepare and to purify resulting in varying physico-chemical properties and to optimize the process for its preparation. It has been noted that compound of formula III is not stable enough to undergo effective purification processes and that previous processes that depended upon purifying the compound of formula III to obtain pure anthranilamides failed to provide such substantially pure anthranilamides and lead to yield loss, as has been made possible by the process of the present invention. Impure compound of formula III on reacting further with methyl amine leads to chlorantraniliprole with various impurities and uneven physical properties and found to be ineffective for the intended use. The present invention finds that purifying the anthranilamides out of an aqueous slurry is a surprisingly better strategy to prepare substantially pure anthranilamides than starting with pure compound of formula III.

Inventors of the present invention noted that, by following the process of the present invention, purification of compound of formula III can be avoided or is not required and chlorantraniliprole could still be obtained that is substantially free from impurities.

The present invention thus provides compounds of Formula (A) that is free from impurities.

Formula A

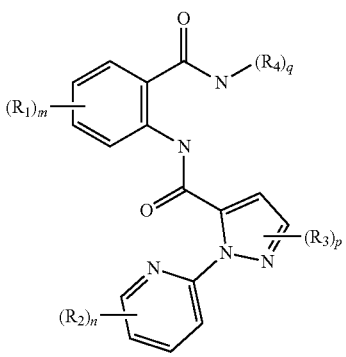

Wherein $R_1$, $R_2$, $R_3$ and $R_4$ can be independently a hydrogen, halogen, cyano, amino, N-thio derivatives, hydroxyl, unsubstituted or substituted linear or branched ($C_1$-$C_{10}$) alkyl or cycloalkyl, heterocyclic unsubstituted or substituted with halogen, cyano, amino, hydorxyl or linear or branched ($C_1$-$C_{10}$) alkyl or linear or branched ($C_1$-$C_{10}$) alkyl and wherein m, n, p and q can be 0, 1, 2, or 3.

In another aspect, the present invention also provides a process for purifying compound of Formula A,

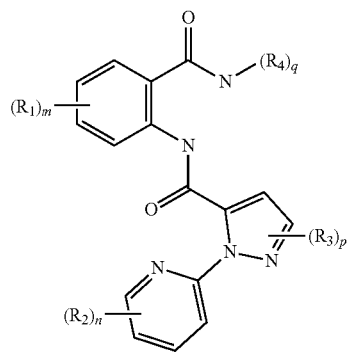

wherein $R_1$, $R_2$, $R_3$ and $R_4$ can be independently a hydrogen, halogen, cyano, amino, N-thio derivatives, hydroxyl, unsubstituted or substituted linear or branched ($C_1$-$C_{10}$) alkyl or cycloalkyl, heterocyclic unsubstituted or substituted with halogen, cyano, amino, hydorxyl or linear or branched ($C_1$-$C_{10}$) alkyl and wherein m, n, p and q can be 0, 1, 2, or 3;

said process comprising purifying the compound of formula A from an aqueous slurry comprising said compound of formula A.

In an embodiment, the aqueous slurry of the compound of formula A is provided in a reactor.

In an embodiment, the aqueous slurry of the compound of formula A comprises a reaction product mixture which comprises the compound of formula A.

In an embodiment, the reaction product mixture is a reaction product of a compound of formula III with methylamine.

In an embodiment, the reaction product mixture is a reaction product of a compound of formula III with methylamine carried out in an organic solvent.

In an embodiment, the compound of formula III is reacted with methylamine without being purified or isolated.

In an embodiment, the aqueous slurry comprises a slurry comprises the reaction product mixture in water.

In an embodiment, purifying the compound of formula A from an aqueous slurry comprising said compound of formula A comprises stirring the aqueous slurry for a predetermined time before purifying said compound of formula A.

In an embodiment, the compound of formula III is a reaction product produced from a reaction between a compound of formula I and a compound of formula II.

In an embodiment, the compound of formula III is a reaction product produced from a reaction between a compound of formula I and a compound of formula II carried out in an organic solvent.

In an embodiment, the compound of formula III is used without being isolated or purified from a reaction between a compound of formula I and a compound of formula II carried out in an organic solvent.

In an embodiment, purifying the compound of formula A from an aqueous slurry comprising said compound of formula A comprises stirring the aqueous slurry for a predetermined time, and subsequently purifying said compound of formula A.

In an embodiment, purifying the compound of formula A from an aqueous slurry comprising said compound of formula A comprises stirring the aqueous slurry for a predetermined time, purifying said compound of formula A, and separating said compound of formula A from the aqueous slurry.

In an embodiment, purifying the compound of formula A from an aqueous slurry comprising said compound of formula A comprises repeatedly: (a) stirring the aqueous slurry for a predetermined time, (b) purifying said compound of formula A, and (c) separating said compound of formula A from the aqueous slurry.

In an embodiment, steps (a), (b) and (c) may be repeated a plurality of times.

In an embodiment, purifying the compound of formula A from an aqueous slurry comprising said compound of formula A comprises stirring the aqueous slurry for a predetermined time, purifying said compound of formula A, separating said compound of formula A from the aqueous slurry, and drying said separated compound of formula A.

In an embodiment, the present invention also provides a process for purifying compound of Formula A,

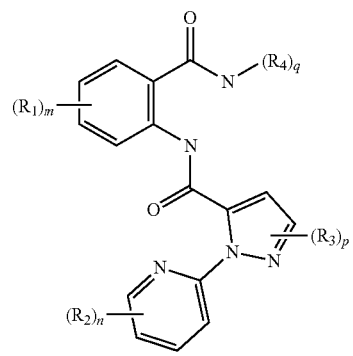

wherein $R_1$, $R_2$, $R_3$ and $R_4$ can be independently a hydrogen, halogen, cyano, amino, N-thio derivatives, unsubstituted or substituted linear or branched ($C_1$-$C_{10}$) alkyl or cycloalkyl, heterocyclic unsubstituted or substituted with halogen, cyano, amino, hydorxyl or linear or branched ($C_1$-$C_{10}$) alkyl and wherein m, n, p and q can be 0, 1, 2, or 3;

said process comprising the steps of:
a) feeding a reaction product mixture comprising compound of Formula A into a reactor;
b) preparing a slurry of the mixture in aqueous conditions;
c) stirring the slurry for a pre-determined time;
d) separating solids;
e) optionally repeating steps b), c) and d); and
f) drying to get purified compound of Formula A.

In an embodiment, the compound of Formula A is when $R_1, R_2, R_3$ and $R_4$ can be independently a hydrogen, halogen, cyano, amino, N-thio derivatives, alkyl, substituted alkyl with halogen, cyano or amino heterocyclic unsubstituted or substituted with halogen, cyano, amino, hydroxyl or linear or branched ($C_1$-$C_{10}$) alkyl compounds wherein m, n, p and q can be 0, 1, 2, or 3.

In one embodiment, the compound of Formula A is when $R_1$ is CN, and $CH_3$, $R_2$ is Cl, $R_3$ is Br and $R_4$ is H and —$CH_3$ wherein m and q=2 as represented in the below structure.

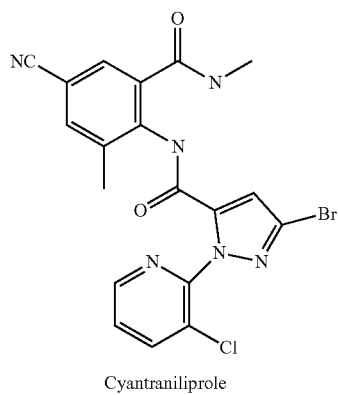 [SMILES: CNC(=O)c1cc(C#N)cc(C)c1NC(=O)c1cc(Br)nn1-c1ncccc1Cl]

Cyantraniliprole

In another embodiment, the compound of Formula A is when $R_1$ is Cl and —$CH_3$, $R_2$ is Cl, $R_3$ is Br and $R_4$ is H and —$CH_3$ wherein m and q=2 as represented in the below structure.

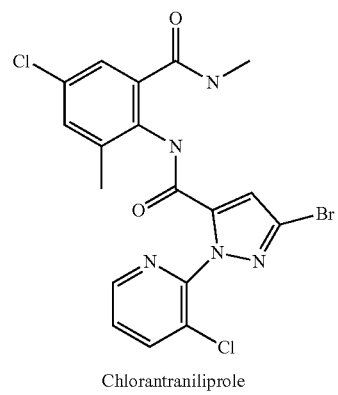 [SMILES: CNC(=O)c1cc(Cl)cc(C)c1NC(=O)c1cc(Br)nn1-c1ncccc1Cl]

Chlorantraniliprole

In another embodiment, the compound of Formula A is when $R_1$ is Cl and Br, $R_2$ is Cl, $R_3$ is Br and $R_4$ is H and 1-cyclopropyl ethyl and wherein m and q=2 as represented in the below structure.

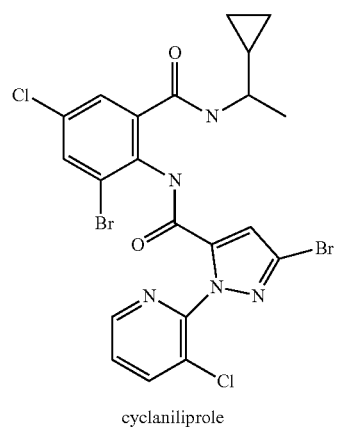 [SMILES: CC(NC(=O)c1cc(Cl)cc(Br)c1NC(=O)c1cc(Br)nn1-c1ncccc1Cl)C1CC1]

cyclaniliprole

In yet another embodiment, the compound of Formula A is when $R_1$ is Cl, $R_2$ is Cl, $R_3$ is Br and $R_4$ is H, and —$CH_3$, wherein m, n and q=2 as represented in the below structure.

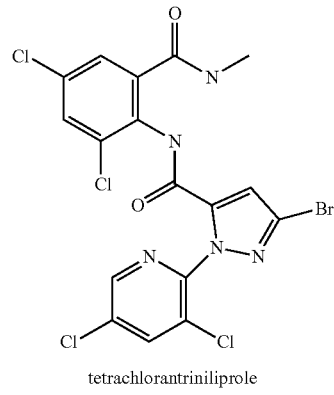 [SMILES: CNC(=O)c1cc(Cl)cc(Cl)c1NC(=O)c1cc(Br)nn1-c1ncc(Cl)cc1Cl]

tetrachlorantriniliprole

In another embodiment, the compound of Formula A is when $R_1$ is CN, and —$CH_3$, $R_2$ is Cl, $R_3$ is 5-(trifluoromethyl)-2H-tetrazol-2-yl] methyl and $R_4$ is H and —$CH_3$ wherein m and q=2 as represented in the below structure.

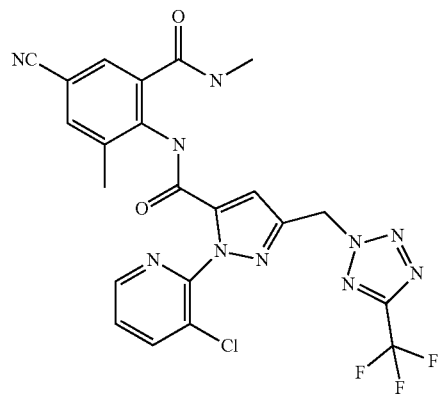

tetraniliprole

In an embodiment, the term 'impurities' refers to unreacted synthetic intermediates, reagents, solvents, organic and/or inorganic products of side reactions, organic and/or inorganic salts and/or other undesired materials.

Therefore, the compounds of the invention being substantially free of impurities is intended to mean the referred compound being substantially free of all the unreacted synthetic intermediates, reagents, solvents, organic and/or inorganic products of side reactions, organic and/or inorganic salts and/or other undesired materials.

In an embodiment, aqueous conditions of step b) refers to water or a mixture of water and one or more solvents.

In a preferred embodiment, aqueous conditions of step b) refers to water.

In an embodiment, slurry of step b) is prepared by mixing reaction mass with water or with a mixture of water and one or more solvents.

In an embodiment, solvents are selected from the group comprising methanol, ethanol n-propanol, n-butanol, acetone, ethyl acetate, dimethyl sulfoxide, acetonitrile and dimethylformamide.

In an embodiment, in step c), the reaction mass is stirred at a temperature from about 25° C. to about 80° C.

In a preferred embodiment, in step c), the reaction mass is stirred at a temperature from about 40° C. to about 60° C.

In an embodiment, in step c), the reaction mass is stirred for a period of at least 15 minutes.

In a preferred embodiment, in step c), the reaction mass is stirred for a period of at least 30 minutes.

In an embodiment, the solid separation of step d) is conducted by filtration, sedimentation, decantation, or by solid-liquid centrifugation.

In a preferred embodiment the solid separation of step d) is conducted by filtration.

The present invention provides chlorantraniliprole substantially free of impurities.

In an embodiment the present invention provides chlorantraniliprole that is substantially free of impurities.

In another embodiment the present invention provides cyantraniliprole that is substantially free of impurities.

In another embodiment the present invention provides chlorantraniliprole with purity >95% by weight.

In another embodiment the present invention provides chlorantraniliprole with purity >97% by weight.

In another embodiment the present invention provides cyantraniliprole with purity >95% by weight.

In another embodiment the present invention provides cyantraniliprole with purity >97% by weight.

In an embodiment, the term 'impurities' refers to unreacted synthetic intermediates, reagents, solvents, organic and/or inorganic products of side reactions, organic and/or inorganic salts and/or other undesired materials.

In another embodiment, synthetic intermediates comprise compound of Formula I, compound of Formula II and compound of Formula III.

In another embodiment, synthetic intermediates comprise compound of Formula I, compound of Formula V and compound of Formula VI.

In an embodiment, reagent include methane sulfonyl chloride and methyl amine.

In an embodiment, the organic and/or inorganic products of side reactions include salts of compound of Formula I with sulfonic acids and/or chlorides.

In an embodiment organic and/or inorganic products of side reactions include salts of compound of Formula I with methane sulfonyl chloride.

In another embodiment organic and/or inorganic products of side reactions include salts of compound of Formula II with sulfonic acids and/or chlorides.

In another embodiment organic and/or inorganic products of side reactions include salts of compound of Formula V with sulfonic acids and/or chlorides.

In yet another embodiment, the present invention provides chlorantraniliprole that is substantially free of compound of Formula I, compound of Formula II, compound of Formula III, salts of compound of Formula I with sulfonic acids and chlorides.

In yet another embodiment, the present invention provides cyantraniliprole that is substantially free of compound of Formula I, compound of Formula V, compound of Formula VI, salts of compound of Formula I with sulfonic acids and chlorides.

In an aspect, the present invention provides a process for purifying chlorantraniliprole, said process comprising purifying Chlorantraniliprole from an aqueous slurry comprising Chlorantraniliprole.

In an embodiment, the aqueous slurry of Chlorantraniliprole is provided in a reactor. In an embodiment, the aqueous slurry of Chlorantraniliprole comprises a reaction product mixture which comprises Chlorantraniliprole.

In an embodiment, the reaction product mixture is a reaction product of a compound of formula III with methylamine.

In an embodiment, the reaction product mixture is a reaction product of a compound of formula III with methylamine carried out in an organic solvent.

In an embodiment, the compound of formula III is reacted with methylamine without being purified or isolated.

In an embodiment, the aqueous slurry comprises a slurry comprises the reaction product mixture in water.

In an embodiment, purifying Chlorantraniliprole from an aqueous slurry comprising Chlorantraniliprole comprises stirring the aqueous slurry for a predetermined time before purifying said Chlorantraniliprole.

In an embodiment, the compound of formula III is a reaction product produced from a reaction between a compound of formula I and a compound of formula II.

In an embodiment, the compound of formula III is a reaction product produced from a reaction between a compound of formula I and a compound of formula II carried out in an organic solvent.

In an embodiment, the compound of formula III is used without being isolated or purified from a reaction between a compound of formula I and a compound of formula II carried out in an organic solvent.

In an embodiment, purifying Chlorantraniliprole from an aqueous slurry comprising Chlorantraniliprole comprises stirring the aqueous slurry for a predetermined time, and subsequently purifying said Chlorantraniliprole.

In an embodiment, purifying Chlorantraniliprole from an aqueous slurry comprising said Chlorantraniliprole comprises stirring the aqueous slurry for a predetermined time, purifying said Chlorantraniliprole, and separating said Chlorantraniliprole from the aqueous slurry.

In an embodiment, purifying Chlorantraniliprole from an aqueous slurry comprising said Chlorantraniliprole comprises repeatedly: (a) stirring the aqueous slurry for a predetermined time, (b) purifying said Chlorantraniliprole, and (c) separating Chlorantraniliprole from the aqueous slurry.

In an embodiment, steps (a), (b) and (c) may be repeated a plurality of times.

In an embodiment, purifying Chlorantraniliprole from an aqueous slurry comprising said Chlorantraniliprole comprises stirring the aqueous slurry for a predetermined time, purifying Chlorantraniliprole, separating Chlorantraniliprole from the aqueous slurry, and drying said separated Chlorantraniliprole.

Thus, the present invention provides a process for purifying chlorantraniliprole, said process comprising the steps of:
a) feeding a reaction product mixture comprising chlorantraniliprole into a reactor;
b) preparing a slurry of the mixture in aqueous conditions;
c) stirring the slurry for a pre-determined time;
d) separating and collecting solids;
e) optionally repeating steps b), c) and d); and
f) drying to get chlorantraniliprole substantially free from impurities.

In an embodiment, chlorantraniliprole of step a) can be prepared from a reaction of compound of Formula I, its derivatives or salts and compound of Formula II, its derivatives or salts.

In an embodiment, aqueous conditions of step b) refers to water or a mixture of water and one or more solvents.

In a preferred embodiment, aqueous conditions of step b) refers to water.

In an embodiment, slurry of step b) is prepared by mixing reaction mass with water or with a mixture of water and one or more solvents.

In an embodiment, in step c), the reaction mass is stirred at a temperature from about 25° C. to about 80° C.

In a preferred embodiment, in step c), the reaction mass is stirred at a temperature from about 40° C. to about 60° C.

In an embodiment, in step c), the reaction mass is stirred for a period of at least 15 minutes.

In a preferred embodiment, in step c), the reaction mass is stirred for a period of at least 30 minutes.

In an embodiment, the solid separation of step d) is conducted by filtration, sedimentation, decantation, or by solid-liquid centrifugation.

In a preferred embodiment the solid separation of step d) is conducted by filtration.

In another embodiment, the present invention provides a process for purifying chlorantraniliprole, said process comprising the steps of:
a) feeding a reaction product mixture comprising chlorantraniliprole into a reactor;
b) preparing a slurry of the mixture in water;
c) stirring the slurry at 25°-60° C. for at least 30 minutes;
d) filtering;
e) optionally repeating steps b), c) and d); and
f) drying to get chlorantraniliprole substantially free from impurities.

In yet another embodiment, the present invention provides a process for purifying chlorantraniliprole, said process comprising the steps of:
a) feeding a reaction product mixture comprising chlorantraniliprole into a reactor;
b) preparing a slurry of the reaction mass in water;
c) stirring at 25°-60° C. for at least 30 minutes;
d) filtering;
e) repeating steps b), c) and d) at least once; and
f) drying to get chlorantraniliprole substantially free from impurities.

The present invention provides a process for preparing chlorantraniliprole that is substantially free from impurities.

The present invention also provides a process preparing chlorantraniliprole that is free from impurities, said process comprising purifying Chlorantraniliprole from an aqueous slurry comprising the reaction product of the compound of formula III with methylamine.

In an embodiment, the aqueous slurry of Chlorantraniliprole is provided in a reactor.

In an embodiment, the aqueous slurry of Chlorantraniliprole comprises a reaction product mixture which comprises Chlorantraniliprole.

In an embodiment, the reaction product mixture is a reaction product of a compound of formula III with methylamine.

In an embodiment, the reaction product mixture is a reaction product of a compound of formula III with methylamine carried out in an organic solvent.

In an embodiment, the compound of formula III is reacted with methylamine without being purified or isolated.

In an embodiment, the aqueous slurry comprises a slurry comprises the reaction product mixture in water.

In an embodiment, purifying Chlorantraniliprole from an aqueous slurry comprising Chlorantraniliprole comprises stirring the aqueous slurry for a predetermined time before purifying said Chlorantraniliprole.

In an embodiment, the compound of formula III is a reaction product produced from a reaction between a compound of formula I and a compound of formula II.

In an embodiment, the compound of formula III is a reaction product produced from a reaction between a compound of formula I and a compound of formula II carried out in an organic solvent.

In an embodiment, the compound of formula III is used without being isolated or purified from a reaction between a compound of formula I and a compound of formula II carried out in an organic solvent.

In an embodiment, purifying Chlorantraniliprole from an aqueous slurry comprising Chlorantraniliprole comprises stirring the aqueous slurry for a predetermined time, and subsequently purifying said Chlorantraniliprole.

In an embodiment, purifying Chlorantraniliprole from an aqueous slurry comprising said Chlorantraniliprole comprises stirring the aqueous slurry for a predetermined time, purifying said Chlorantraniliprole and separating said Chlorantraniliprole from the aqueous slurry.

In an embodiment, purifying Chlorantraniliprole from an aqueous slurry comprising said Chlorantraniliprole comprises repeatedly: (a) stirring the aqueous slurry for a predetermined time, (b) purifying said Chlorantraniliprole, and (c) separating Chlorantraniliprole from the aqueous slurry.

In an embodiment, steps (a), (b) and (c) may be repeated a plurality of times.

In an embodiment, purifying Chlorantraniliprole from an aqueous slurry comprising said Chlorantraniliprole comprises stirring the aqueous slurry for a predetermined time, purifying Chlorantraniliprole, separating Chlorantraniliprole from the aqueous slurry, and drying said separated Chlorantraniliprole.

The present invention provides a process for purifying cyantraniliprole, said process comprising purifying cyantraniliprole from an aqueous slurry of cyantraniliprole.

The present invention provides a process for purifying cyantraniliprole said process comprising the steps of:
a) feeding a reaction product mixture comprising cyantraniliprole into a reactor;
b) preparing a slurry of the mixture in aqueous conditions;
c) stirring the slurry for a pre-determined time;
d) separating solids;
e) optionally repeating steps b), c) and d); and
f) drying to get purified cyantraniliprole.

In an embodiment, the present invention provides a process for preparing chlorantraniliprole that is substantially free from impurities, said process comprising the steps of:
  a) reacting compound of Formula III and methyl amine in an organic solvent;
  b) separating and collecting solids;
  c) preparing a slurry of step b) product in aqueous conditions;
  d) stirring for a pre-determined time;
  e) separating and collecting solids;
  f) optionally repeating steps c), d) and e); and
  g) drying to get chlorantraniliprole substantially free from impurities.

In an embodiment, reaction of step a) is conducted in an organic solvent selected from the group comprising acetonitrile, tetrahydrofuran, ethyl acetate, toluene, xylene and dioxane.

In a preferred embodiment reaction of step a) is conducted in ethyl acetate.

In an embodiment, in step a) methyl amine is used as an aqueous solution.

In an embodiment, aqueous conditions of step c) refers to water or a mixture of water and one or more solvents.

In a preferred an embodiment, aqueous conditions of step c) refers to water.

In an embodiment, slurry of step c) is prepared by mixing reaction mass with water or with a mixture of water and one or more solvents.

In an embodiment, in step d), the reaction mass is stirred at a temperature from about 25° C. to about 80° C.

In a preferred embodiment, in step d), the reaction mass is stirred at a temperature from about 40° C. to about 60° C.

In an embodiment, in step d), the reaction mass is stirred for a period of at least 15 minutes.

In a preferred embodiment, in step d), the reaction mass is stirred for a period of at least 30 minutes.

In an embodiment, the solid separation of step e) is conducted by filtration, sedimentation, decantation, or by solid-liquid centrifugation.

In a preferred embodiment the solid separation of step e) is conducted by filtration.

The present invention also provides a process for preparing chlorantraniliprole that is substantially free from impurities, said process comprising purifying Chlorantraniliprole from an aqueous slurry, said aqueous slurry comprising a hydrophilic solvent admixed with the reaction product of a compound of formula III with methylamine.

In an embodiment, hydrophilic solvents are selected from the group comprising methanol, ethanol n-propanol, n-butanol, acetone, ethyl acetate, dimethyl sulfoxide, acetonitrile and dimethylformamide.

In a preferred embodiment, the present invention provides a process for preparing chlorantraniliprole that is substantially free from impurities, said process comprising the steps of:
  a) reacting compound of Formula III and aqueous methyl amine solution in an organic solvent;
  b) filtering the reaction mass;
  c) preparing a slurry of the reaction mass in water;
  d) stirring at 25°-60° C. for at least 30 minutes;
  e) filtering;
  f) repeating steps c), d) and e) at least once; and
  g) drying to get purified chlorantraniliprole.

The present invention further provides a process for preparing chlorantraniliprole that is substantially free from impurities wherein purification of compound of Formula III is not essential.

The present invention provides a process for preparing chlorantraniliprole that is substantially free from impurities, said process comprising the steps of:
  a) preparing compound of Formula III by reacting compound of Formula I and compound of Formula II in an organic solvent;
  b) optionally purifying compound of Formula III;
  c) reacting compound of Formula III with methyl amine in an organic solvent;
  d) separating and collecting solids;
  e) preparing a slurry of step d) product in aqueous conditions;
  f) stirring the slurry for a pre-determined time;
  g) separating and collecting solids;
  h) optionally repeating steps e), f) and g); and
  i) drying to get chlorantraniliprole substantially free from impurities.

In an embodiment, reaction of step a) is conducted in an organic solvent selected from the group comprising acetonitrile, tetrahydrofuran, ethyl acetate, toluene, xylene and dioxane.

In another embodiment reaction of step a) is conducted in presence of a base.

In an embodiment, step b) purification of compound of Formula III can be optional.

In another embodiment, in step (b), compound of Formula III can be purified partially.

In yet another embodiment, according to the present invention, purification of compound of Formula III is not essential.

In an embodiment, step b) purification of compound of Formula III can be avoided. In an embodiment, the process of the present invention leads to chlorantraniliprole that is substantially free from impurities which are produced during step a) reaction.

In another embodiment, the process of the present invention avoids the purification of less stable compound of Formula III.

In an embodiment, reaction of step c) is conducted in an organic solvent selected from the group comprising acetonitrile, tetrahydrofuran, ethyl acetate, toluene, xylene and dioxane.

In a preferred embodiment reaction of step c) is conducted in ethyl acetate.

In an embodiment, in step c) methyl amine is used as an aqueous solution.

In an embodiment, aqueous conditions of step e) refers to water or a mixture of water and one or more solvents.

In a preferred an embodiment, aqueous conditions of step e) refers to water.

In an embodiment, slurry of step e) is prepared by mixing reaction mass with water or with a mixture of water and one or more solvents.

In an embodiment, in step f), the reaction mass is stirred at a temperature from about 25° C. to about 80° C.

In a preferred embodiment, in step f), the reaction mass is stirred at a temperature from about 40° C. to about 60° C.

In an embodiment, in step f), the reaction mass is stirred for a period of at least 15 minutes.

In a preferred embodiment, in step f), the reaction mass is stirred for a period of at least 30 minutes.

In an embodiment, the solid separation of step g) is conducted by filtration, sedimentation, decantation, or by solid-liquid centrifugation.

In a preferred embodiment the solid separation of step g) is conducted by filtration.

In an embodiment, the present invention provides Chlorantraniliprole having a purity of at least about 97.0%.

In an embodiment, the present invention provides Chlorantraniliprole having a purity of at least about 97.5%.

In an embodiment, the present invention provides an anthranilamide insecticide having less than 0.5% of intermediates of formulae I, II, and III.

In an embodiment, the present invention provides an anthranilamide insecticide having less than 0.2% of intermediates of formulae I, II and III.

In an embodiment, the present invention provides Chlorantraniliprole having less than 0.5% of intermediates of formulae I, II, and III.

In an embodiment, the present invention provides Chlorantraniliprole having less than 0.2% of intermediates of formulae I, II and III.

In an embodiment, the present invention provides an anthranilamide insecticide having less than 1.0% of the salts of intermediates of formulae I, II, and III.

In an embodiment, the present invention provides an anthranilamide insecticide having less than 0.5% of the salts of intermediates of formulae I, II and III.

In an embodiment, the present invention provides Chlorantraniliprole having less than 1.0% of the salts of intermediates of formulae I, II, and III.

In an embodiment, the present invention provides Chlorantraniliprole having less than 0.5% of the salts of intermediates of formulae I, II and III.

In these embodiments, the salts of intermediates of formulae I, II or III includes the salts of these intermediates of methane sulfonyl chloride.

In an embodiment, the present invention provides an anthranilamide insecticide having less than 2.0% of the inorganic impurities.

In an embodiment, the present invention provides an anthranilamide insecticide having less than 0.5% of the inorganic impurities.

In an embodiment, the present invention provides Chlorantraniliprole having less than 2.0% of the inorganic impurities.

In an embodiment, the present invention provides Chlorantraniliprole having less than 0.5% of the inorganic impurities.

The present invention further provides a process for preparing cyantraniliprole that is free from impurities, said process comprising the steps of:
a) reacting compound of Formula VI with methyl amine in an organic solvent;
b) separating and collecting solids;
c) preparing a slurry of step b) product in aqueous conditions;
d) stirring the slurry for a pre-determined time;
e) separating and collecting solids;
f) optionally repeating steps c), d) and e); and
g) drying to get cyantraniliprole substantially free from impurities.

The present invention further provides a process for preparing cyantraniliprole said process comprising purifying cyantraniliprole from an aqueous slurry, said aqueous slurry comprising a hydrophilic solvent admixed with the reaction product of a compound of formula VI with methylamine.

The advantages and other parameters of the present invention is illustrated by the below given examples. However, the scope of the present invention is not limited by the examples in any manner. It will be appreciated by any person skilled in this art that the present invention includes aforesaid examples and further can be modified and altered within the technical scope of the present invention.

EXAMPLES

Example 1: Preparation of Compound of Formula III

Methane sulphonyl chloride (56 g) in acetonitrile (108 g) was added to the mixture of compound of Formula I (54 g), compound of Formula II (35 g) and pyridine (73 g) in acetonitrile (162 g) with stirring at 5-10° C. followed by stirring for 3 hours at 25° C. The mixture was then filtered and washed with acetonitrile followed by drying to get compound of Formula III (75 g, Yield=93%)

Example 2: Preparation of Chlorantraniliprole

Compound of Formula III (75 g) was stirred in ethyl acetate (225 g) in a reactor at 15-20° C. while stirring. Aqueous solution of methyl amine (43 g) was added to the reaction mixture in 2 hours at 15-25° C. and stirred for 3 hours. The mass was then cooled to 30° C., filtered and washed with ethyl acetate to get chlorantraniliprole (98 g, 93% purity).

Example 3: Purification of Chlorantraniliprole 98 g of chlorantraniliprole (as prepared in example 2) and 200 g of water were charged into a reactor. The mass was stirred at 40°-50° C. for one hour. The mass was then filtered. The wet mass was then charged into the reactor and 200 g of water was added. The slurry was then stirred at 40°-50° C. for one hour. The mass was then filtered and washed with hot water. The wet mass thus obtained was dried at 70° C. 51 g, purity 97.5%.

Example 4: Preparation of Compound of Formula III

Methane sulphonyl chloride (56 g) in Tetrahydrofuran (75 g) was added to the mixture of compound of Formula I (54 g), compound of Formula II (35 g) and pyridine (73 g) in Tetrahydrofuran (75 g) with stirring at 5-10° C. followed by stirring for 3 hours at 25° C. The mixture was then filtered and washed with acetonitrile followed by drying to get compound of Formula III (68 g, Yield=84.3%)

Example 5: Preparation of Chlorantraniliprole

Compound of Formula III (68 g) was stirred in ethyl acetate (175 g) in a reactor at 15-20° C. while stirring. Aqueous solution of methyl amine (41 g) was added to the reaction mixture in 2 hours at 15-25° C. and stirred for 3 hours. The mass was then cooled to 30° C., Add 200 gms water and maintain for 1 hr then filtered and washed with ethyl acetate to get chlorantraniliprole (58 g, 93% purity).

Example 6: Purification of Chlorantraniliprole 58 g of chlorantraniliprole (as prepared in example 5) 200 g of water and 100 g of ethyl acetate were charged into a reactor. The mass was stirred at 40°-50° C. for one hour. The mass was then filtered and washed with hot water. The wet mass thus obtained was dried at 70° C. 49 g, purity 97.5%.

Example 7: Analytical Results of Chlorantraniliprole Prepared and Purified by Process According to the Present Invention The analytical results of chlorantraniliprole prepared (Example 2) and purified (Example 3) by the present invention is presented in the below table (Table 1):

TABLE 1

| Sample | Chlorantraniliprole (% purity) | Intermediates (%) | Salts of intermediates (%) | Inorganics (%) | Others (%) |
|---|---|---|---|---|---|
| Example 2 | 93 | 0.5-1 | 1-2 | 2-4 | <1 |
| Example 3 | >97 | <0.2 | <0.5 | <0.5 | <0.1 |

Intermediates include compound of Formula I, compound of Formula II and compound of Formula III. Salts of intermediates include salt of compound of Formula I with methane sulfonyl chloride. Inorganics include chlorides. Traces of solvents, bases and other unidentified impurities are also getting removed by the process of the present invention. From the above experiments it is established that the process according to the present invention can be used to produce chlorantraniliprole of high purity as well as consistent properties.

Example 8: Preparation of Compound of Formula VI

Methane sulphonyl chloride (60 g) in acetonitrile (115 g) was added to the mixture of compound of Formula I (55 g), compound of Formula V (38 g) and pyridine (75 g) in acetonitrile (165 g) with stirring at 5-10° C. followed by stirring for 4 hours at 25° C. The mixture was then filtered and washed with acetonitrile followed by drying to get compound of Formula VI (73 g, Yield=92%)

Example 9: Preparation of Cyantraniliprole (Formula VII)

Compound of Formula VI (73 g) was stirred in ethyl acetate (220 g) in a reactor at 15-20° C. while stirring. Aqueous solution of methyl amine (43 g) was added to the reaction mixture in 2 hours at 15-25° C. and stirred for 3 hours. The mass was then cooled to 30° C., filtered and washed with ethyl acetate to get cyantraniliprole (95 g, 93% purity).

Example 10: Purification of Cyantraniliprole (Formula VII)

95 g of cyantraniliprole (as prepared in example 6) and 200 g of water were charged into a reactor. The mass was stirred at 35°-40° C. for one hour. The mass was then filtered. The wet mass was then charged into the reactor and 200 g of water was added. The slurry was then stirred at 35°-40° C. for one hour. The mass was then filtered and washed with hot water. The wet mass thus obtained was dried at 70° C. (49 g, purity 97.5%).

The invention claimed is:

1. A process for purifying chlorantraniliprole, said process comprising:
   a) preparing an aqueous slurry of a reaction product mixture comprising chlorantraniliprole in aqueous conditions, wherein the reaction product mixture is formed by a reaction of a compound of formula III

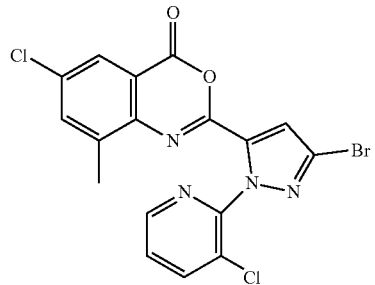

Formula III with methylamine in an organic solvent selected from the group consisting of acetonitrile and ethyl acetate;
   b) stirring the aqueous slurry at a temperature from 40° C. to 50° C. for one hour;
   c) separating solids from the aqueous slurry;
   d) optionally repeating steps a), b) and c); and
   e) drying the solids to obtain a purified chlorantraniliprole having a purity of at least 97% from the reaction product mixture, wherein the aqueous slurry comprises water or a mixture of water and ethyl acetate admixed with the reaction product mixture to solubilize the impurities.

2. The process for purifying chlorantraniliprole according to claim 1,
   wherein the compound of Formula III is prepared by reacting a compound of Formula I and a compound of Formula II in an organic solvent selected from the group comprising acetonitrile, tetrahydrofuran, and ethyl acetate.

* * * * *